United States Patent [19]

Hughes

[11] Patent Number: 5,217,019
[45] Date of Patent: Jun. 8, 1993

[54] APPARATUS AND METHOD FOR CONTINUOUSLY MONITORING CARDIAC OUTPUT

[75] Inventor: Timothy J. Hughes, Palo Alto, Calif.

[73] Assignee: Abbott Laboratories, Abbott Park, Ill.

[21] Appl. No.: 815,068

[22] Filed: Dec. 27, 1991

[51] Int. Cl.$^5$ .............................. A61B 5/02; A61B 5/00
[52] U.S. Cl. ..................................... 128/668; 128/695; 128/713; 128/736
[58] Field of Search ................. 128/668, 691, 692–695, 128/713, 736; 73/204.17, 204.23, 204.25

[56] References Cited

U.S. PATENT DOCUMENTS

| | | | |
|---|---|---|---|
| 3,359,974 | 12/1967 | Khalil | 128/2.05 |
| 3,519,924 | 7/1970 | Burton | 73/204.23 X |
| 3,988,928 | 11/1976 | Edstrom et al. | 73/204.23 X |
| 4,059,982 | 11/1977 | Bowman | 73/204.17 X |
| 4,236,527 | 12/1980 | Newbower et al. | 128/692 |
| 4,332,157 | 1/1982 | Zemel et al. | 73/204.23 X |
| 4,361,049 | 11/1982 | Volgyesi | 128/713 X |
| 4,403,615 | 9/1983 | Hoehner | 128/713 X |
| 4,501,145 | 2/1985 | Boegli et al. | 73/204.17 |
| 4,507,974 | 4/1985 | Yelderman | 73/861.06 |
| 4,542,748 | 9/1985 | Roy | 128/713 |
| 4,637,253 | 1/1987 | Sekimura et al. | 73/204.23 X |
| 4,745,928 | 5/1988 | Webler et al. | 128/736 X |
| 4,819,655 | 4/1989 | Webler | 128/713 |
| 4,821,568 | 4/1989 | Kiske | 73/204.17 |
| 4,841,981 | 6/1989 | Tanabe et al. | 128/713 X |
| 4,979,514 | 12/1990 | Sekii et al. | 128/713 |
| 4,993,420 | 2/1991 | Welkowitz et al. | 128/668 |
| 5,080,106 | 1/1992 | Sekii et al. | 128/692 |
| 5,101,828 | 4/1992 | Welkowitz et al. | 128/668 |

FOREIGN PATENT DOCUMENTS 9117703 11/1991 World Int. Prop. O. .......... 128/713

OTHER PUBLICATIONS

Philip, James H., et al., "Continuous Thermal Measurement of Cardiac Output," *IEEE Transactions on Biomedical Engineering*, vol. BME-31, No. 5, May 1984, pp. 393–400.

*Primary Examiner*—Randall L. Green
*Assistant Examiner*—Elizabeth M. Burke
*Attorney, Agent, or Firm*—Christensen, O'Connor, Johnson & Kindness

[57] ABSTRACT

A method and apparatus for continuously monitoring cardiac output based upon the phase shift between an input signal and a temperature signal indicative of the change in temperature of blood leaving the heart. In a first preferred embodiment of a cardiac output monitoring system (10), a catheter (14) is provided with an electrical resistance heater (22). An electrical current having a sinusoidal wave form with a period of from 30 to 60 seconds is applied to the heater, causing power to be dissipated into the blood within a patient's heart (12). A temperature sensor (24) disposed near a distal end of the catheter produces a signal indicative of the temperature of blood leaving the heart. The temperature signal and the signal corresponding to the electrical power dissipated in the heater (an input signal) are filtered at a frequency $\omega$ corresponding to the frequency of the applied electrical current, i.e., the frequency of the input signal. The amplitude of the input power, the amplitude of the temperature signal, and their phase difference are used in calculating cardiac output. In another embodiment, a temperature conditioned saline solution (84) is circulated through catheter (14') in a closed loop, so that it flows through a heat exchanger (60) disposed within the heart. The fluid is circulated through the catheter on a periodic basis, providing a periodic input signal. The temperature signal produced by the temperature sensor on the catheter distal end and power dissipated to or absorbed from the blood by the heat exchanger comprise the two signals from which the cardiac output is determined as described above. The determination of cardiac output is also corrected for the time constant of the catheter/heater (or heat exchanger) and of the temperature sensor.

11 Claims, 4 Drawing Sheets

APPARATUS AND METHOD FOR CONTINUOUSLY MONITORING CARDIAC OUTPUT

FIELD OF THE INVENTION

This invention generally pertains to apparatus and a method for monitoring the volumetric output of a heart, and more specifically, to apparatus and a method for making this determination by using an injectateless technique that changes the temperature of blood in the heart.

BACKGROUND OF THE INVENTION

Cardiac output, the volumetric rate at which blood is pumped through the heart, is most often determined clinically by injecting a bolus of chilled saline or glucose solution into the right auricle or right ventricle through a catheter. A thermistor disposed in the pulmonary artery is used to determine a temperature-time washout curve as the chilled injectate/blood mixture is pumped from the heart. The area under this curve provides an indication of cardiac output. Although this thermo-dilution method can give an indication of cardiac output at the time the procedure is performed, it cannot be used for continuously monitoring cardiac output. Moreover, the frequency with which the procedure is performed is limited by its adverse effects on a patient, including the dilution of the patient's blood that occurs each time the chilled fluid is injected. In addition, the procedure poses an infection hazard to medical staff from blood contact, and to the patient, from exposure to possibly contaminated injectate fluid or syringes.

Alternatively, blood in the heart can be chilled or heated in an injectateless method by a heat transfer process using a temperature-conditioned fluid that is pumped in a closed loop, toward the heart through one lumen within the catheter and back through another lumen. The principal advantages of using such a non-injectate heat transfer process to change the temperature of blood are that the blood is not diluted, and the temperature differential between the blood and the heat exchanger is much less compared to the temperature differential between an injectate fluid and blood in the typical thermal dilution procedure.

U.S. Pat. No. 4,819,655 (Webler) discloses an injectateless method and apparatus for determining cardiac output. In Webler's preferred embodiment, a saline solution is chilled by a refrigeration system or ice bath and introduced into a catheter that has been inserted through a patient's cardiovascular system into the heart. The catheter extends through the right auricle and right ventricle and its distal end is disposed just outside the heart in the pulmonary artery. A pump forces the chilled saline solution through a closed loop fluid path defined by two lumens in the catheter, so that heat transfer occurs between the solution and blood within the heart through the walls of the catheter. A thermistor disposed at the distal end of the catheter monitors the temperature of blood leaving the heart, both before the chilled fluid is circulated through the catheter to define a baseline temperature, and after the temperature change in the blood due to heat transfer with the chilled saline solution has stabilized. Temperature sensors are also provided to monitor both the temperature of the chilled saline solution at or near the point where it enters the catheter (outside the patient's body) and the temperature of the fluid returning from the heart. In addition, the rate at which the chilled solution flows through the catheter is either measured or controlled to maintain it at a constant value. Cardiac output (CO) is then determined from the following equation:

$$CO = \frac{\dot{V}_I(\Delta T_I)}{C(\Delta T_B)} \quad (1)$$

where $\dot{V}_I$ equals the rate at which the chilled fluid is circulated through the catheter; $\Delta T_I$ equals the difference between the temperature of the chilled fluid input to the catheter and the temperature of the fluid returning from the heart; $\Delta T_B$ equals the difference between the temperature of the blood leaving the heart before the chilled fluid is circulated and the temperature of the blood leaving the heart after the chilled fluid is circulated (after the temperature stabilizes); and C is a constant dependent upon the blood and fluid properties. The patent also teaches that the fluid may instead be heated so that it transfers heat to the blood flowing through the heart rather than chilled to absorb heat.

U.S. Pat. No. 4,819,655 further teaches that the cardiac monitoring system induces temperature variations in the pulmonary artery that are related to the patient's respiratory cycle and are therefore periodic at the respiratory rate. Accordingly, Webler suggests that the signal indicative of $T_B'$ (the temperature of the chilled blood exiting the heart) should be processed through a Fourier transform to yield a period and amplitude for the respiratory cycle, the period or multiples of it then being used as the interval over which to process the data to determine cardiac output.

Another problem recognized by Webler is the delay between the times at which circulation of the chilled fluid begins and the temperature of the blood in the pulmonary artery reaches equilibrium, which is caused by the volume of blood surrounding the catheter in the right ventricle and in other portions of the heart. The patent suggests introducing a generally corresponding delay between the time that temperature measurements are made of the blood before the chilled fluid is circulated and after, for example, by waiting for the $\Delta T_B$ value to exceed a level above that induced by respiratory variations. However, for a relatively large volume heart and/or very low cardiac output, the $T_B'$ data do not reach equilibrium in any reasonable period of time. The quantity of blood flowing through the large volume heart represents too much mixing volume to accommodate the technique taught by Webler for processing the data to determine cardiac output. As a result, the measurement period for equilibrium must be excessively long to reach equilibrium, thereby introducing a potential error in the result due to either a shift in the baseline temperature of the blood or changes in the cardiac output. For this reason, the technique taught by Webler to determine cardiac output using the data developed by his system is not practical in the case of large blood volumes in the heart and/or low cardiac outputs.

The technique disclosed by Webler also assumes that all of the energy absorbed by a chilled fluid (or lost by a heated fluid) represents heat transferred between the fluid and the blood in the heart. This assumption ignores the heat transfer that occurs between the fluid and the mass of the catheter. A somewhat smaller source of error arises due to the energy required to change the temperature of the small thermal mass of the thermistor bead that monitors the temperature of blood leaving the heart. For long measurement periods, these errors can generally be ignored. In addition, if the thermistor bead is selected to have a very small mass and fast response time, its error contribution may be insignificant. However, as the measurement period becomes shorter, the effect of these error sources becomes increasingly more important.

Instead of cooling (or heating) the blood in the heart by heat transfer with a circulating fluid to determine cardiac output, the blood can be heated with an electrical resistance heater that is disposed on a catheter inserted into heart. The apparatus required for this type of injectateless cardiac output measurement is significantly less complex than that required for circulating a fluid through the catheter. An electrical current is applied to the resistor through leads in the catheter and adjusted to develop sufficient power dissipation to produce a desired temperature rise signal in the blood. However, care must be taken to avoid using a high power that might damage the blood by overheating it. An adequate signal-to-noise ratio is instead preferably obtained by applying the electrical current to the heater at a frequency corresponding to that of the minimum noise generated in the circulatory system, i.e., in the range of 0.02 through 0.15 Hz. U.S. Pat. No. 4,236,527 (Newbower et al.) describes such a system, and more importantly, describes a technique for processing the signals developed by the system to compensate for the above-noted effect of the mixing volume in the heart and cardiovascular system of a patient, even one with a relatively large heart. (Also see J. H. Philip, M. C. Long, M. D. Quinn, and R. S. Newbower, "Continuous Thermal Measurement of Cardiac Output," IEEE Transactions on Biomedical Engineering, Vol. BMI 31, No. 5, May 1984.)

Newbower et al. teaches modulating the thermal energy added to the blood at two frequencies, e.g., a fundamental frequency and its harmonic, or with a square wave signal. Preferably, the fundamental frequency equals that of the minimal noise in the cardiac system. The temperature of the blood exiting the heart is monitored, producing an output signal that is filtered at the fundamental frequency to yield conventional cardiac output information. The other modulation frequency is similarly monitored and filtered at the harmonic frequency, and is used to determine a second variable affecting the transfer function between the injection of energy into the blood and the temperature of the blood in the pulmonary artery. The amplitude data developed from the dual frequency measurements allows the absolute heart output to be determined, thereby accounting for the variability of fluid capacity or mixing volume.

Newbower et al. does not address correcting for errors due to the thermal mass of the catheter and the thermistor bead used to monitor the temperature of blood leaving the heart. Furthermore, the technique taught in Newbower et al. requires matching the dual frequency data to a predefined curve using a best fit algorithm, to determine the absolute cardiac output. Accordingly, the results are not as accurate as may be desired, particularly in the presence of noise.

It is preferable that a non-injectate method for determining cardiac output be based on measured output data processed using a technique that does not require fitting the output data to a curve. Cardiac output should also be determined by a method that compensates for the mixing volume of the heart, regardless of its relative size, and also compensates for the thermal mass of the catheter and the thermistor bead used to produce the output signal. The foregoing aspects and many of the attendant advantages of the present invention will become more readily appreciated as the same becomes better understood by reference to the following detailed description, when taken in conjunction with the accompanying drawings.

SUMMARY OF THE INVENTION

In accordance with the present invention, apparatus are provided for continuously monitoring a cardiac output of a heart. The apparatus include a catheter having a plurality of lumens that extend generally between a proximal end and a distal end. The distal end of the catheter is insertable into the heart through a cardiovascular system. Means are also included for supplying a periodically varying, temperature modifying input signal to a portion of the catheter that is spaced apart from its distal end. A blood temperature sensor is disposed adjacent the distal end of the catheter and produces a blood temperature signal that is indicative of a temperature of blood flowing from the heart. Means are operative to determine power transferred by the temperature modifying input signal, producing a corresponding periodically varying power signal that is indicative of the power transferred. A phase comparator determines a difference in phase between the periodically varying power signal and the periodically varying temperature signal. Control means then determine the cardiac output of the heart as a function of the power signal, the blood temperature signal, and the difference in phase between said signals.

Preferably, the means for supplying the periodically varying temperature modifying signal comprise a source of an electrical current connected by a plurality of leads to a resistor disposed on a portion of the catheter that is spaced apart from its distal end. The input signal comprises a periodically varying electrical current that is applied to heat the resistor and any blood around the resistor. The means for determining power transferred comprise means for determining the power dissipated in the resistor by the electrical current flowing through it.

Alternatively, the means for supplying the periodically varying temperature modifying signal comprise a pump that delivers a temperature-conditioned fluid through a closed loop fluid flow path defined by the lumens in the catheter. The pump cycles on and off periodically at a predefined frequency. For this embodiment, the means for determining power transferred comprise a first temperature sensor that monitors the temperature of the temperature-conditioned fluid pumped into the catheter, a second temperature sensor that monitors the temperature of the temperature-conditioned fluid as it returns from the heart, and means for determining the rate of flow of said temperature-conditioned fluid. The control means determine the power transferred as a function of the difference in temperature of the temperature-conditioned fluid monitored by the first and the second temperature sensors, and the rate of flow of the temperature-conditioned fluid in the catheter.

Instead of being chilled, the temperature-conditioned fluid may be heated substantially above a normal temperature of blood entering the heart.

The cardiac output is defined by the following equation:

$$CO = |P(\omega)| * COS\ \Delta\Phi / (|T(\omega)| * Cb) \qquad (2)$$

where:
CO = the cardiac output;
P(ω) = the power transferred by the input signal, which varies at a frequency ω;
ΔΦ = the difference in phase between the power signal and the blood temperature signal;
T(ω) = the blood temperature indicated by the blood temperature signal, which varies at the frequency ω; and
Cb = a specific heat times density constant for the blood.
The apparatus further comprises filter means for filtering the power signal and the blood temperature signal to remove frequencies different from the frequency at which the input signal periodically varies. In addition, the control means compensate for an attenuation of the blood temperature signal by the catheter and the blood temperature sensor, in determining the cardiac output.

DETAILED DESCRIPTION OF THE PREFERRED EMBODIMENT

Figure 1:
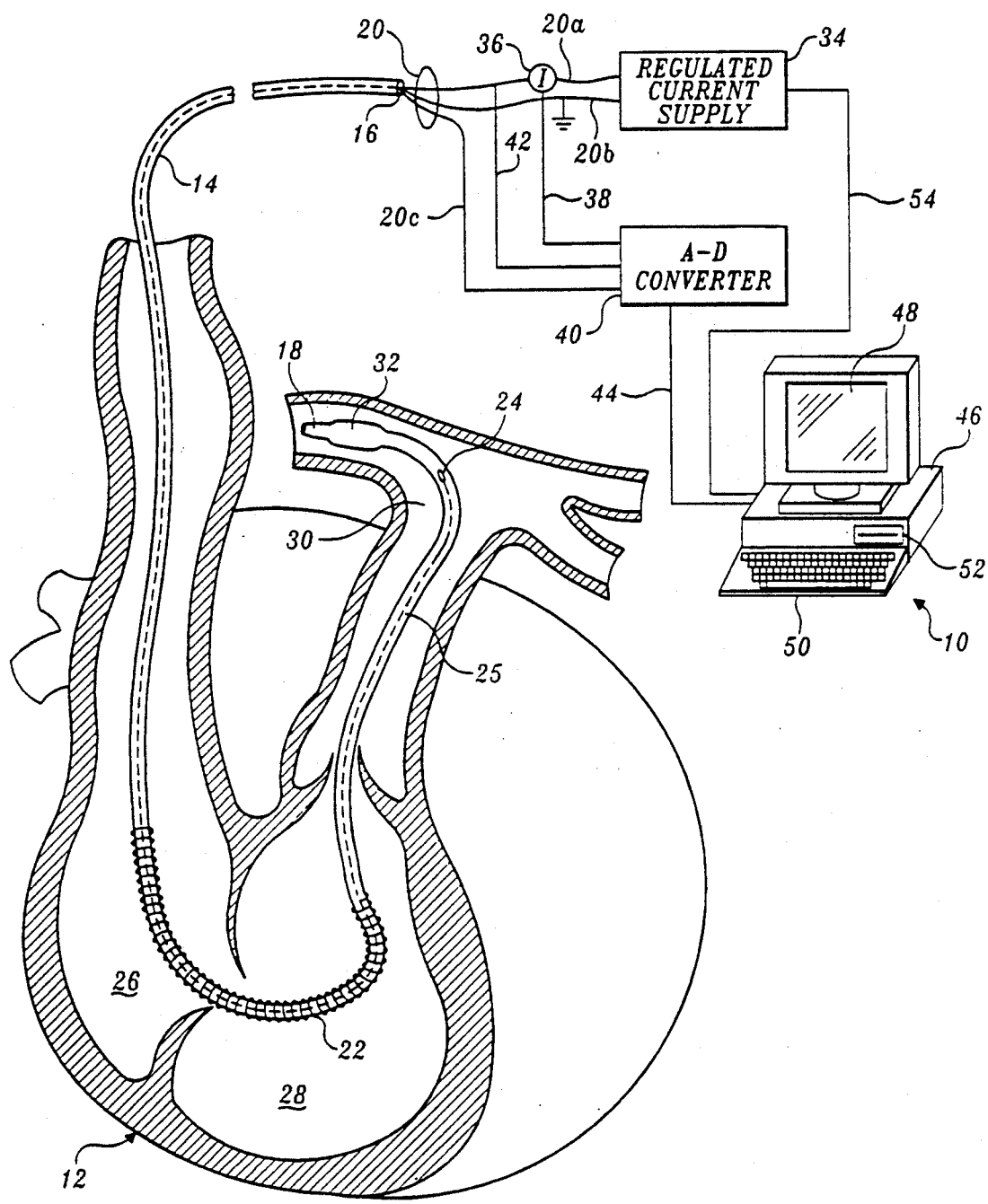
FIG. 1 is a block diagram of a first embodiment of the present invention, illustrating the disposition of a catheter and electrical resistance heater within a human heart that is cut away to more clearly show the right auricle, ventricle, and pulmonary artery.

A first embodiment of a cardiac output monitoring system in accordance with the present invention is shown generally in FIG. 1 at reference numeral 10. A human heart 12 is schematically illustrated in this figure, with a portion of the heart cut away to show the disposition of a catheter 14 that is inserted through a patient's cardiovascular system and into heart 12. Catheter 14 has a proximal end 16 and a distal end 18. A plurality of leads 20 extend longitudinally through catheter 14 (within lumens that are not separately shown) and include leads 20a and 20b that carry an electrical current to an electrical resistance heater 22. In the preferred form of the invention, heater 22 comprises a coil of insulated copper, stainless steel, nickel, or nichrome wire approximately 12 cm in length that is wound around catheter 14 approximately 10 to 15 cm from distal end 18. Heater 22 has a nominal resistance of from 15 to 30 ohms. Leads 20c are connected to a temperature sensor 24, which is spaced apart from distal end 18 and generally mounted on the external surface of the catheter so that it can readily sense the temperature of blood flowing past the distal end as the blood is pumped from heart 12.

As shown clearly in FIG. 1, catheter 14 extends through a right auricle 26, a right ventricle 28, and into a pulmonary artery 30 of the patient whose cardiac output is being monitored. Adjacent distal end 18 is disposed a balloon 32, which is inflated to float distal end 18 upwardly from right ventricle 28 into pulmonary artery 30. Heater 22 can be positioned entirely within right auricle 26, or as shown, may extend from right auricle 26 into right ventricle 28.

A regulated current supply 34 supplies a periodic electrical current used to generate heat in a sinusoidal wave form at heater 22, at a voltage ranging from 10 to 25 volts peak amplitude. Alternatively, a square wave current supply can be used. As the current flows through the wire coil comprising heater 22, it produces heat in proportion to the $I^2R$ losses in the heater (where I is the current and R is the resistance of the heater). The heat produced is transferred to the blood within right auricle 26 and right ventricle 28. A current sensor 36 produces a signal indicative of the magnitude of the electrical current flowing through lead 20a to heater 22, and this signal is input through leads 38 to analog-to-digital (A-D) converters 40. A second input to A-D converters 40 is a voltage signal that indicates the voltage developed across heater 22; this voltage signal is conveyed by a lead 42. The third input to the A-D converters comprises the signal indicative of the temperature of the blood leaving heart 12, produced by temperature sensor 24, connected to leads 25, which comprise the distal end of leads 20c. Digitized signals from A-D converters 40 are conveyed through leads 44 to input ports (not separately shown) on a portable computer 46.

Associated with portable computer 46 is a video display 48 on which data defining the cardiac output of heart 12 are displayed, along with other data and information. A keyboard 50 is connected to portable computer 46 to provide for input and user control of the cardiac output measurement. In addition, portable computer 46 includes a hard drive or floppy drive 52 that is used for magnetic storage of data, test results, and programs such as the software controlling the measurement of cardiac output. Portable computer 46 controls regulated current supply 34 by supplying control signals transmitted through leads 54 that extend between the regulated current supply and the portable computer.

The electrical current that energizes heater 22 to heat the blood flowing through heart 12 is supplied either in the form of a sine wave having a 30- to 60-second period, or as a square wave with an energized period ranging between 15 and 30 seconds (followed by a like duration during which no current is supplied). The power developed by heater 22 thus represents a periodic input signal, whereas the signal developed by temperature sensor 24 comprises an output signal indicative of the temperature of the blood leaving the heart. To determine power dissipated within heater 22, the digitized signals indicative of the current flowing through the heater and voltage drop across it are multiplied together by portable computer 46. The power dissipated within heater 22 to heat the blood flowing through heart 12, i.e., the peak to peak amplitude, is therefore easily determined and is defined as the "input signal" for purposes of the following discussion. Accordingly, the power applied, which represents the input signal, and the temperature of the blood exiting the heart through the pulmonary artery, which represents the output signal, are used in the first preferred embodiment to determine the cardiac output of heart 12, as explained below.

Figure 2:
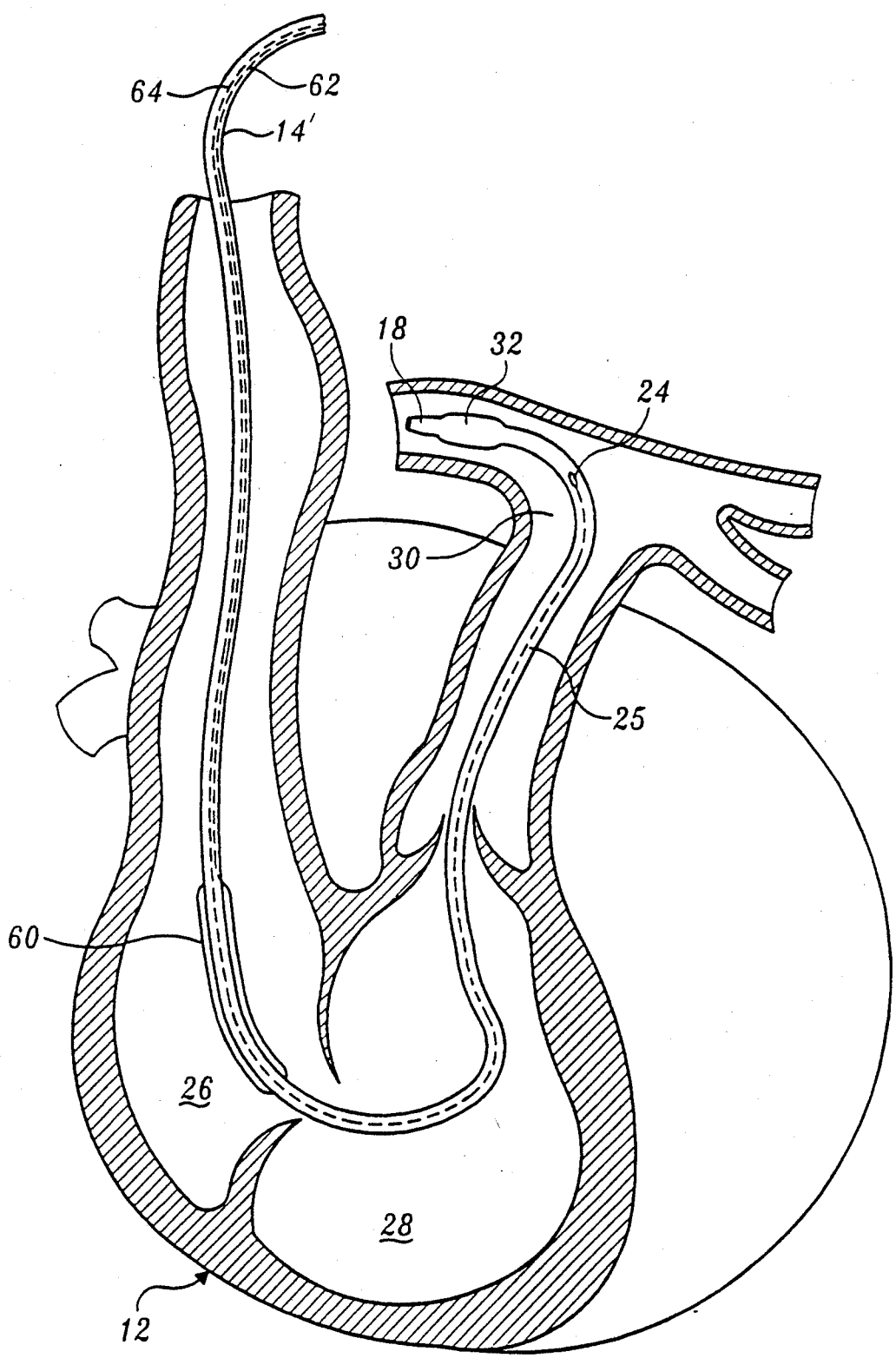
FIG. 2 is a cut away view of a human heart, showing the disposition of a catheter through which a temperature-conditioned fluid is circulated to change the temperature of the blood within the heart.

An alternative embodiment for developing an input signal and an output signal that can be used to determine the cardiac output of heart 12 is shown in FIG. 2. In this embodiment, a catheter 14' is used to convey a cooling or heating fluid to a heat exchanger 60 formed on the catheter, set back from its distal end so that the heat exchanger is within right auricle 26. Two lumens (not separately shown) within catheter 14' define a supply fluid path 62 through which a liquid cooled to a temperature well below that of the body temperature of the patient is conveyed to heat exchanger 60, and a return fluid path 64 through which the fluid is then returned back to a source of the fluid, external to the patient's body. In most other aspects of its configuration and use, catheter 14' is similar to catheter 14, shown in FIG. 1. Like catheter 14, catheter 14' includes temperature sensor 24 disposed adjacent its distal end 18 so that it is positioned within pulmonary artery 30.

Instead of cooling a fluid to a temperature lower than the temperature of blood entering heart 12 through catheter 14', the fluid may be heated above the temperature of the blood so that it transfers heat to the blood, just as heater 22 does. In either case, whether the input signal cools the blood or heats it, the cardiac output measurement system changes the temperature of blood in the heart on a periodic basis so that the output signal produced by temperature sensor 24 changes periodically in response thereto. Furthermore, the change in the temperature of blood flowing from the heart, i.e., the output signal, is phase shifted relative to the input signal due to the time required to change the temperature of the mass of blood within the right auricle and right ventricle.

Figure 3:
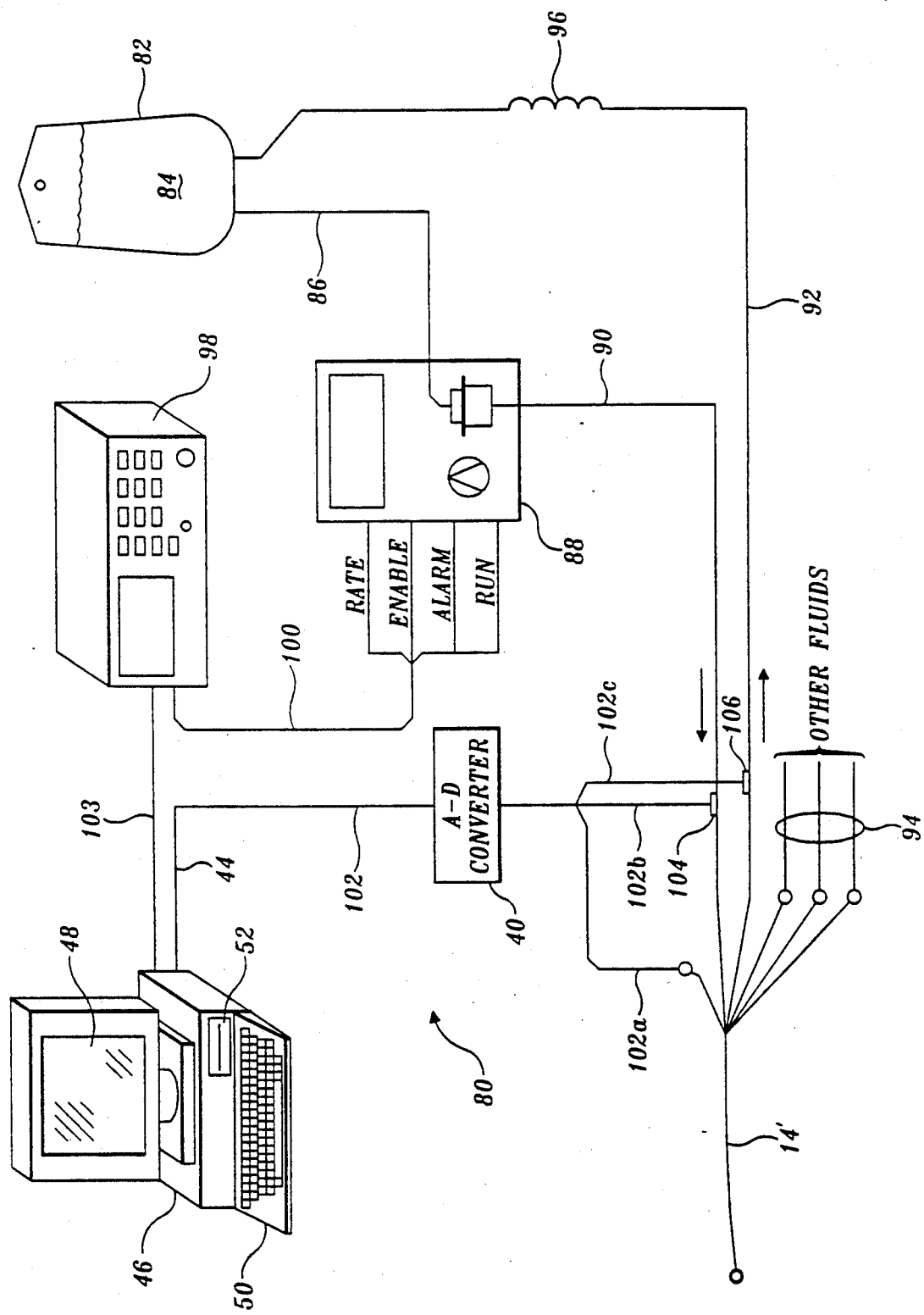
FIG. 3 is a block diagram of a cardiac output measurement system used in connection with a noninjectate system that changes the temperature of blood in the heart by heat exchange with a fluid circulated through a catheter in a closed loop.

In FIG. 3, the remainder of a cardiac output measurement system 80, which is used for circulation of a temperature conditioned fluid (with respect to the temperature of blood entering heart 12) through catheter 14' is illustrated schematically. Cardiac output measurement system 80 includes a reservoir 82 (hanger bag) of a saline solution 84. Saline solution 84 flows under the influence of gravity through a line 86 to a pump 88. When energized for periods of 15 to 30 seconds at a time, pump 88 forces saline solution 84 through a supply line 90, which is connected to supply fluid path 62 within catheter 14'. After the liquid flows through catheter 14' and exchanges heat with blood within heart 12 at heat exchanger 60, it flows back along return fluid path 64 into a return line 92. Return line 92 passes through an external heat exchanger 96, which reduces the temperature of the returning saline solution to ambient temperature, e.g., 24° C. Thereafter, the returning saline solution flows back into reservoir 82 for recirculation by pump 88.

The operation of pump 88 is controlled by a pump control 98, which is connected to the pump by leads 100 that convey signals determining the rate at which pump 88 operates. In addition, leads 100 carry an ENABLE signal that energizes pump 88 and signals indicative of any alarm condition, e.g., air in the line or restriction of lines 86 or 90. Pump control 98 also receives a signal from pump 88 indicating that the pump is running, to confirm that fluid is being delivered to the catheter as expected.

It will be appreciated that instead of using liquid at ambient temperature to cool the blood flowing through the heart, saline solution 84 can be chilled to a much cooler temperature (using a chiller coil disposed downstream of pump 88, in heat transfer relationship with supply line 90). For example, saline solution 84 can be chilled to a lower than ambient temperature by heat transfer with ice water at 0° C.; or, a more elaborate evaporative refrigerant chiller coil can be employed that uses a refrigerant fluid to cool saline solution 84 as the refrigerant fluid undergoes expansion. Similarly, it is also possible to provide heat transfer between saline solution 84 that is circulated through catheter 14' and a heated liquid or to provide heat from some other source so that the saline solution entering catheter 14' is elevated in temperature above the temperature of blood entering heart 12.

Pump control 98 is controlled by portable computer 46 so that pump 88 is enabled on a periodic basis to circulate temperature conditioned saline solution 84 through catheter 14'. In this embodiment, the input signal to the blood within the heart is represented by the flow of temperature conditioning liquid through catheter 14'. A signal applied to pump control 98 over lines 103, which connect the pump control to the portable computer, is used to enable the operation of pump 88. The flow of temperature-conditioned saline solution 84 through catheter 14' is enabled for 15 to 30 seconds, then turned off for an equivalent interval, and this cyclic operation is continued during the measurement of cardiac output.

A plurality of lines 102 carry signals indicative of various temperatures to A-D converters 40, which supplies the corresponding digitized signals to portable computer 46. Specifically, a line 102a is connected to lead 20c, and thus conveys the signal indicative of the temperature of blood leaving heart 12 to A-D converters 40. A lead 102b is connected to a temperature sensor 104 that produces a signal indicative of the temperature of saline solution 84 flowing into supply fluid path 62 within catheter 14'. Similarly, a temperature sensor 106 is connected to a lead 102c, which conveys a signal indicative of the temperature of saline solution 84 returning from catheter 14' into return line 92. A plurality of fluid lines 94 are connected to other lumens within catheter 14' and can be used to inject medication into the heart and inflate balloon 32 during the insertion of catheter 14' into heart 12.

Figure 4:
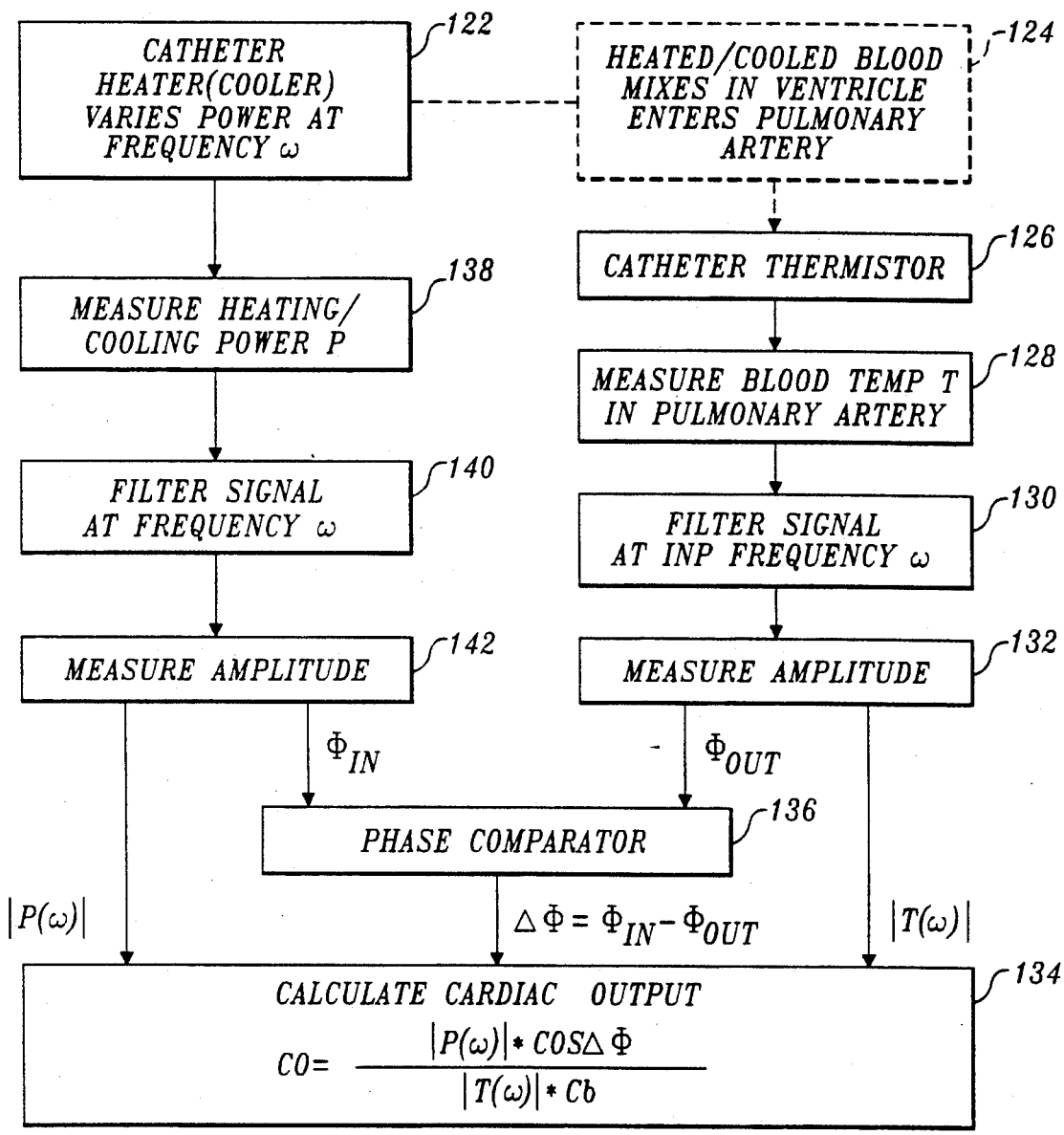
FIG. 4 is a flow chart showing the logical steps used in determining cardiac output in accordance with the present invention.

As noted in the Background of the Invention, the present invention enables cardiac output to be determined continuously rather than intermittently (an unfortunate limitation of the conventional injectate thermal dilution technique) and is much less prone to noise than previous continuous cardiac output monitoring methods. In the present invention, cardiac output is determined by portable computer 46 following the logical steps shown in a flow chart 120, in FIG. 4. Starting at a block 122, the temperature of blood flowing through heart 12 is modified by applying the input signal, e.g., by electrical current to heater 22, or by initiating the flow of a temperature-conditioned fluid through catheter 14' so that heat is transferred at heat exchanger 60—in either case, thereby modifying the temperature of blood within the heart. The transfer of heat to or from blood within heart 12 occurs at a frequency ω, as shown in block 122. This frequency is selected to minimize the noise caused by patient respiration.

A dashed-line block 124 indicates that the blood heated or cooled by the input signal mixes with the other blood in right ventricle 28 and enters pulmonary artery 30. A block 126 refers to temperature sensor 24, which produces the signal that is indicative of the temperature of blood exiting heart 12. With reference to a block 128, the blood temperature T within pulmonary artery 30 comprises the output signal that is digitized by A-D converter 40. The digitized signal indicative of the temperature of blood within the pulmonary artery is filtered at the input frequency $\omega$, as indicated in a block 130 in FIG. 4.

In the preferred embodiment, the output signal is filtered by portable computer 46. Specifically, a discrete Fourier transform is performed on the digitized output signal to transform the signal from the time domain into the frequency domain. The portion of the transformed signal at the input frequency $\omega$ is thus determined and comprises a filtered output signal. By filtering the output signal (and the input signal, as described below), noise at other frequencies is substantially eliminated. Alternatively, an analog bandpass filter circuit could be used to process the input signal before it is digitized, in lieu of the discrete Fourier transform. Other types of digital filtering could also be used to eliminate noise components at other frequencies.

After the output signal is filtered, the amplitude of the filtered output signal is determined, as noted in a block 132. Portable computer 46 uses the peak to peak value of the filtered output signal for this amplitude, represented by $|T(\omega)|$. The value $|T(\omega)|$ is then used in a block 134 for calculating cardiac output. Since the filtered output signal is a periodically varying signal, it has a phase relationship that is represented by the value $\Phi_{out}$ (used as described below).

The left side of flow chart 120 is directed to the steps used in processing the input signal. As shown in a block 138, the heating or cooling power P, which represents the heat transferred to or absorbed from the blood in the heart, is determined. As described above, the heating power of heater 22 is determined from the product of the electrical current flowing through it and the voltage drop across the heater, as well known to those of ordinary skill in the art.

If catheter 14' is used and heat is transferred between the circulated saline solution and blood flowing through heart 12, the input signal is determined as a function of: (a) the temperature differential between the saline solution supplied to catheter 14' and that returning from the catheter, measured at temperature sensors 104 and 106, and (b) the saline solution flow rate provided by pump 88. In the preferred form of the invention shown in FIG. 3, pump 88 is set to provide a flow rate of approximately 1.5 liters per hour when energized. The input signal (representing input power P) is determined by portable computer 46 from the digitized signals indicative of the saline solution temperatures at temperature sensors 104 and 106, the flow rate of the saline solution through the catheter (predefined or measured), and the specific heat of the saline solution, as will be apparent to those of ordinary skill in the art.

Portable computer 46 then filters the input signal at the input frequency $\omega$, as indicated in a block 140. To filter the input signal, the portable computer processes it with a discrete Fourier transform, converting it from the time domain to the frequency domain. The portion of the transformed signal at the frequency $\omega$ comprises the filtered input signal. The filtered input signal has both a phase and amplitude. In a block 142, the amplitude of the input signal is determined and is input to block 134 as $|P(\omega)|$. The phase of this filtered input signal, $\Phi_{in}$, is compared to the phase of the output signal in a block 136, producing a differential phase $\Delta\Phi$, which is equal to the difference between $\Phi_{in}$ and $\Phi_{out}$. Portable computer 46 determines the differential phase and as shown in block 134, calculates cardiac output "CO" as follows:

$$CO = |P(\omega)| * COS\Delta\Phi / (|T(\omega)| * Cb) \qquad (3)$$

In the above equation, the value Cb is the product of specific heat and density of blood.

The volume of blood within right ventricle of heart 12, i.e., the mixing volume, is estimated from the following expression:

$$V = \frac{\tau |P(\omega)| \sqrt{\frac{1}{(COS(\Delta\Phi))^2} - 1}}{2\pi Cb |T(\omega)|} \qquad (4)$$

where $\tau$ is the period of the input signal. To reduce the effects of phase noise on the determination of cardiac output, an estimation of mixing volume can be made from Equation 4 and used in the following relationship:

$$CO = \sqrt{\left(\left(\frac{|P(\omega)|}{Cb|T(\omega)|}\right)^2 - (\omega \overline{V})^2\right)} \qquad (5)$$

The estimate of mixing volume is preferably averaged over a long term (assuming that volume is relatively constant over the time during which cardiac output is determined), yielding an average mixing volume, $\overline{V}$, which is used in Equation 5 to determine cardiac output. The resulting determination of cardiac output from Equation 5 is therefore less sensitive to phase noise, including heart rate variations.

When a heat signal is injected into the blood within heart 12, either by cooling the blood or by applying heat to it, a transport delay time is incurred before the input heat signal reaches temperature sensor 24 in the pulmonary artery. The transport delay time adds a phase shift that is flow rate and vessel size dependent. The phase error due to transport delay time is defined as:

$$\Delta\Phi_{error} = \frac{\pi R^2 \omega L}{1000 * CO} \qquad (6)$$

where L is equal to the length of the path from the point of which the heat signal is injected into the blood within the heart to the point at which the temperature sensor is disposed (in cm), R is the vessel radius (in cm), and CO is the cardiac output in liters/second. For example, a typical phase shift would be approximately 28.8° for a path 10 cm in length, with a rate of flow of one liter per minute, a radius of 1.6 cm, and a period for the injection of the heat signal equal to 60 seconds.

The phase shift introduced by transport delay becomes significant at relatively low flow rates, making accurate correction for the mixing volume difficult. One way to address this problem is to apply the input signal at two (or more) different frequencies, enabling a separate estimate of transport delay phase shift and mixing volume phase shift to be determined from the difference in phase shift at the different frequencies.

There are two additional sources of error for which corrections can be applied in determining cardiac output. The sources of error relate to the time constant for the catheter and thermistor caused by their respective thermal masses. The thermal mass of the catheter attenuates and phase shifts the input signal, whereas the thermal mass of temperature sensor 24 attenuates and phase shifts the received temperature signal corresponding to the change in temperature in the blood flowing past temperature sensor 24. The correction used in the preferred embodiment assumes a simple first-order system. For example, heater 22 is assumed to have a time constant $T_{htr}$ (actually the time constant is for the catheter and heater), and temperature sensor 24 to have a time constant $T_{sens}$, both of which are empirically determined. Cardiac output is then determined from:

$$CO = \frac{|P(\omega)|*\cos(\Phi_{in} - \Phi_{out} - \Phi_{htr} - \Phi_{sens})*HTR_{atten}*SENSOR_{atten}}{|T(\omega)|*Cb} \quad (7)$$

where:
$\Phi_{htr} = -\text{ARCTAN}(\omega*T_{htr})$;
$\Phi_{sens} = -\text{ARCTAN}(\omega*T_{sens})$;
$HTR_{atten} = \cos(\Phi_{htr})$; and
$SENSOR_{atten} = \cos(\Phi_{sens})$.

Equation 7 recognizes that a time delay occurs between the arrival at temperature sensor 24 of blood having a different temperature due to the input of a heat signal and the change in the output signal of the temperature sensor. Similarly, the thermal mass of the catheter/heater introduces a time delay between the application of the input signal and the transfer of energy into the blood around heater 22 (or heat exchanger 60). Typical time constants for both heater 22 and temperature sensor 24 are approximately two seconds each. Based on the assumption that the time constants for these two elements do not vary with flow rate, amplitude errors and thus cardiac output errors introduced from this source of error, should be constant. dependent only on the frequency of the input signal. Accordingly, the phase shift introduced by these time constants should also be constant. Since the sensitivity to phase errors increases at low flow rates and large mixing volumes, it is important to correct for the phase shift due to the time constants of the catheter/heater (or heat exchanger) and temperature sensor, at large overall phase angles.

While the preferred embodiment of the invention has been illustrated and described, it will be appreciated that various changes can be made therein without departing from the spirit and scope of the invention. Accordingly, it is not intended that the scope of the present invention be in any way limited by the disclosure of the preferred embodiment, but instead that it be determined entirely by reference to the claims that follow.

The embodiments of the invention in which an exclusive property or privilege is claimed are defined as follows:

1. Apparatus for continuously monitoring a cardiac output of a heart, comprising:
   (a) a catheter having a plurality of lumens that extend generally between a proximal end and a distal end of the catheter, the distal end of the catheter being insertable into a heart through a cardiovascular system;
   (b) means for supplying a periodically varying, temperature modifying input signal to a portion of the catheter that is spaced apart from its distal end;
   (c) a blood temperature sensor disposed adjacent the distal end of the catheter, said temperature sensor being provided to produce a blood temperature signal that is indicative of a temperature of blood flowing from the heart;
   (d) means for determining power transferred by the temperature modifying input signal, said means for determining producing a corresponding periodically varying power signal that is indicative of said power transferred, which corresponds to the input signal;
   (e) a phase comparator for determining a difference in phase between the periodically varying power signal and the periodically varying temperature signal; and
   (f) control means for determining the cardiac output of the heart as a function of the power signal, the blood temperature signal, and the difference in phase between said signals.

2. The apparatus of claim 1, wherein the means for supplying comprise a source of an electrical current connected by a plurality of leads to a resistor disposed in the portion of the catheter spaced apart from its distal end, said input signal comprising a periodically varying electrical current that is applied to heat the resistor and any blood around the resistor.

3. The apparatus of claim 2, wherein the electrical current flowing through the resistor dissipates power and wherein the means for determining power transferred comprise means for determining the power dissipated in the resistor by the electrical current flowing through it.

4. The apparatus of claim 1, wherein the means for supplying comprise a pump that delivers a temperature-conditioned fluid through a closed loop fluid flow path defined by the lumens of the catheter, said pump cycling on and off periodically at a predefined frequency.

5. The apparatus of claim 4, wherein the means for determining power transferred comprise a first temperature sensor that monitors a temperature of the temperature-conditioned fluid pumped into the catheter, a second temperature sensor that monitors a temperature of the temperature-conditioned fluid as it returns from the heart, and means for determining a rate of flow of said fluid, the control means determining the power transferred as a function of the difference in temperature of the temperature-conditioned fluid monitored by the first and the second temperature sensors, and of the rate of flow of the temperature-conditioned fluid in the catheter.

6. The apparatus of claim 4, wherein the means for supplying further comprise a fluid chiller that cools the temperature conditioned fluid substantially below a temperature of blood entering the heart.

7. The apparatus of claim 4, wherein the fluid is heated substantially above a normal temperature of blood entering the heart.

8. The apparatus of claim 1, wherein the cardiac output is defined by an equation as follows:

$$CO = |P(\omega)|*COS\Delta\Phi/(|T(\omega)|*Cb)$$

where:
CO = the cardiac output;
$P(\omega)$ = the power transferred by the input signal, which varies at an angular frequency $\omega$;
$\Delta\Phi$ = the difference in phase between the power signal and the blood temperature signal;

$T(\omega)$ = the blood temperature indicated by the blood temperature signal, which varies at the angular frequency $\omega$; and $Cb$ = a specific heat times density constant for the blood.

9. The apparatus of claim 1, further comprising bandpass filter means for filtering the power signal and the blood temperature signal to filter out frequencies different from a frequency at which the input signal periodically varies.

10. The apparatus of claim 1, further comprising means for compensating for a phase shift error in the blood temperature signal due at least in part to a thermal mass of the catheter.

11. The apparatus of claim 1, wherein the control means compensate for an attenuation of the blood temperature signal by the catheter and the blood temperature sensor, in determining the cardiac output.

* * * * *